US00PP11092P

United States Patent [19]

White et al.

[11] Patent Number: Plant 11,092

[45] Date of Patent: Oct. 12, 1999

[54] APPLE TREE NAMED 'SCIEARLY'

[76] Inventors: Allan White, HortResearch, Goddards Lane, Havelock North, New Zealand; Donald McKenzie, deceased, late of Havelock North, New Zealand; Joy McKenzie, P.O. Box 8345, Havelock North, New Zealand, legal representative of said Donald W McKenzie, deceased

[21] Appl. No.: 08/906,764

[22] Filed: Aug. 5, 1997

[51] Int. Cl.[6] ..... A01H 5/00

[52] U.S. Cl. ..... Plt./161

[58] Field of Search ..... Plt./34.1, 161

[56] References Cited

PUBLICATIONS

UPOV CD–Rom, 98/01, Apple named 'Sciearly', PBR APP088, New Zealand, 1993.

*Primary Examiner*—Howard J. Locker
*Assistant Examiner*—Melissa L. Kimball
*Attorney, Agent, or Firm*—Quarles & Brady LLP

[57] ABSTRACT

The new and distinct variety is a selection from seedlings derived from crossing the apple varieties known as 'Gala' (U.S. Plant Pat. No. 3,637) and 'Splendour' (U.S. Plant Pat. No. 2,460). The fruit of the apple tree of this new variety has an attractive appearance characterized by its early harvest season, large fruit size, and overall dark red block color pattern. The new variety has been named 'Sciearly'.

1 Drawing Sheet

SUMMARY OF THE INVENTION

The new *Malus domestica* variety was selected from a population of seedlings derived from crossing the apple varieties 'Splendour' (U.S. Plant Pat. No. 2,460) and 'Gala' (U.S. Plant Pat. No. 3,637) in 1984. The new variety was distinguishable from the parent varieties Splendour and Gala as well as the sister varieties 'Sciray' (U.S. Plant Pat. No. 7,815); 'Sciglo' (U.S. Plant Pat. No. 7,813); 'Sciros' (U.S. Plant Pat. No. 7,814) and 'Scired' (U.S. Plant Pat. No. 08/687,874). The features which distinguish the new variety from the aforementioned varieties are:

Gala: Sciearly fruit has earlier harvest season, larger size, and a block color pattern compared to the striped color pattern of Gala.

Splendour: Sciearly fruit has earlier harvest season, firmer flesh, and thicker skin.

Sciray: Sciearly fruit has block color pattern of dark red color compared to the light red striping of Sciray.

Sciglo: Sciearly has earlier harvest season and larger fruit size.

Sciros: Sciearly has an earlier harvest season, redder color, and rounder fruit shape.

Scired: Sciearly fruit has rounder shape, earlier season, and less skin russeting.

The new variety has been named the 'Sciearly' variety. Asexual propagation shows that the unique combination of characteristics come true to form and are established and transmitted through succeeding propagation. In order to obtain true-to-type clones of the initial plant, the breeders asexually propagated plants by budding dormant buds from the original seedling onto MM106 root stock.

BRIEF DESCRIPTION OF THE DRAWINGS

The accompanying drawings show typical specimens of the foliage and fruit of the new variety as depicted in colors as nearly true as is reasonably possible to make the same in a color illustration of this character.

In FIG. 1, at the upper left hand, is a top view of an apple of the variety, while at the upper right hand is a bottom view of the apple of the variety. In FIG. 1, at the lower left hand is a side view of the apple of the variety, while in the lower right hand is a cross-sectional view of an apple of the variety.

DETAILED DESCRIPTION OF THE DISCLOSURE

Figure 1:
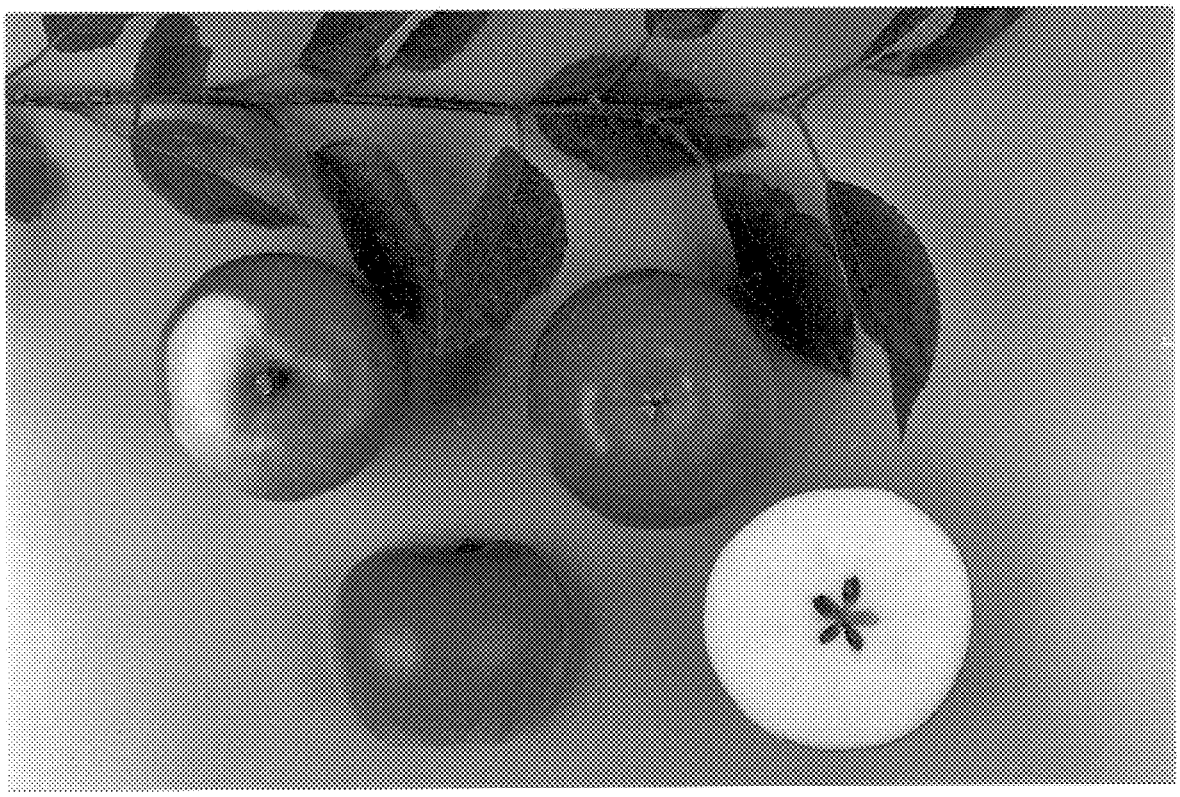
FIG. 1 represents four views of an apple and foliage of the new variety.

The following is a detailed description of the new variety with color terminology in accordance with The Royal Horticultural Society Colour Charts (R.H.S.C.C.).

The specimens described were grown at Havelock North, New Zealand. The observations were made in the 1996 season on trees which were eight years old at the time.

Tree: Medium; spreading habit; bearing on shoots and spurs; medium vigor on MM106 rootstock.

Trunk: Moderately rough; size, medium; brown; 166A when new, 165B when mature.

Branches: Thin; moderately rough; moderate branching; large crotch angles, 30–60°; approximately 5 spurs/10 cm on 3 year old wood; length of annual growth, 80–100 cm.

Lenticels: Average numbers; large size.

Leaves: Medium size; upward pose; average length, 9.1 cm; average width, 4.4 cm; large length/width ratio of blade; upfolded to concave shape in cross section; serrate indentation of margin; medium glossiness of upper side; weak pubescence on lower side; medium petiole length, 2.8 cm; medium stipule size, medium time of bud burst. The color of the blade is green, 139A.

Flowers: Medium time of beginning of flowering (10% flowers), blossom commenced about October 5, full bloom occurs about October 10; medium size; flat shape; margin of petals, overlapping; color of bud just before flower opens, pink, 63C.

Fruit: Examined at optimum maturity. The fruit ripens for eating in the early season. Harvest commences about February 5 and ends about February 30 in Hawkes Bay, New Zealand.

Size: Large to very large; average width, 7.6 cm; average height, 6.2 cm; average weight, 203 gms.

Shape: Short, globose, conical, symmetric in side view, ribbing absent; medium degree of crowning at distil end.
Cavity: Medium depth, 1.2 cm; medium width, 3.6 cm.
Basin: Medium depth, 0.91 cm; medium width, 2.8 cm.
Stem: Thick (comparable to Cox's Orange Pippin, an unpatented variety); medium to long length, 2.2 cm.
Sepal: Length, medium; spacing, touching.
Eye: Size, medium; aperture, closed.
Skin: Smooth; bloom of skin, absent; greasiness of skin, absent; cracking tendency of skin, absent; thickness, medium; background color, yellow-green 4C; lenticels, medium size.
Over Color: Approximately 80% of skin surface; dark red solid flush, 46A; low amount of russet around stalk cavity.
Flesh: Juicy; medium firmness; yellowish, 10D; crisp; weak browning of flesh 1 hour after cutting.
Texture: Medium.
Flavor: Strong sweetness, medium acidity, mild aroma, milder flavor than Gala.
Quality: Excellent for fresh consumption.
Core: Distinctness of core line in cross section (median through locules), medium; aperture of locules in cross section, open.
Sinus: Closed.
Seeds: Five locules; 8 to 10 seeds total, 2 seeds per locule maximum; seeds of medium size, 0.9 cm long, 0.5 cm wide; form obtuse; color dark brown, 175B.
Use: Dessert.
Keeping quality: Very good. No significant disorders after 100 days storage.
Resistance to pests and diseases: Medium susceptibility to major pests and diseases of apple.
Production: Early and regular cropping, very good fruit size even when carrying a large crop. No biennial bearing observed. Trees require pruning in winter to create an open tree structure for good light interception.
Pollinator: No specific pollinator is required, but cross pollination is necessary since the plant cannot efficiently pollinate itself.

It is claimed:

1. A new and distinct variety of apple tree which was selected from seedlings derived from crossing the apple varieties known as 'Splendour' (U.S. Plant Pat. No. 2,460) and 'Gala' (U.S. Plant Pat. No. 3,637) substantially as shown and described, characterized by its early harvest season, large fruit size and overall dark red color and sweet flavor.

* * * * *